(12) United States Patent
Perreault et al.

(10) Patent No.: US 7,491,213 B2
(45) Date of Patent: Feb. 17, 2009

(54) CATHETER SHAFT HAVING DISTAL SUPPORT

(75) Inventors: Daniel Perreault, Bellevue, WA (US);
Douglas A. Devens, Jr., Saint Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 761 days.

(21) Appl. No.: 10/757,683

(22) Filed: Jan. 13, 2004

(65) Prior Publication Data

US 2005/0154414 A1 Jul. 14, 2005

(51) Int. Cl.
*A61M 29/00* (2006.01)
(52) U.S. Cl. .................. 606/194; 604/103.04
(58) Field of Classification Search .............. 604/96.01, 604/99.04, 509, 525–527, 103, 99.01, 103.09, 604/164.01, 103.04; 606/191, 194, 192
See application file for complete search history.

(56) References Cited

U.S. PATENT DOCUMENTS

| | | | |
|---|---|---|---|
| 4,819,751 A | | 4/1989 | Shimada et al. |
| 4,955,895 A | * | 9/1990 | Sugiyama et al. ........... 606/194 |
| 5,040,548 A | | 8/1991 | Yock |
| 5,042,985 A | | 8/1991 | Elliott et al. |
| 5,078,727 A | | 1/1992 | Hannam et al. |
| 5,176,637 A | * | 1/1993 | Sagae ..................... 604/103.14 |
| 5,209,728 A | | 5/1993 | Kraus |
| 5,328,468 A | | 7/1994 | Kaneko et al. |
| 5,330,429 A | | 7/1994 | Noguchi et al. |
| 5,338,295 A | | 8/1994 | Cornelius et al. |
| 5,370,615 A | | 12/1994 | Johnson |
| 5,385,562 A | | 1/1995 | Adams et al. |
| 5,425,712 A | | 6/1995 | Goodin |
| 5,437,632 A | | 8/1995 | Engelson |
| 5,460,608 A | | 10/1995 | Lodin et al. |
| 5,512,051 A | | 4/1996 | Wang et al. |

(Continued)

FOREIGN PATENT DOCUMENTS

WO    WO 03/035159 A2    5/2003

(Continued)

OTHER PUBLICATIONS

U.S. Appl. No. 10/309,466 to John J. Chen et al., filed Dec. 4, 2002.

*Primary Examiner*—Nicholas D Lucchesi
*Assistant Examiner*—Theodore J Stigell
(74) *Attorney, Agent, or Firm*—Crompton, Seager & Tufte LLC

(57) ABSTRACT

A catheter comprising an inflatable balloon having a proximal end, a distal end, and an inflation cavity therebetween, a catheter shaft having the inflatable balloon affixed proximate a distal end thereof, the catheter shaft having an inflation lumen fluidly connected to the balloon inflation cavity. A guidewire lumen extends through the balloon cavity within a tubular member which is affixed to the inflatable balloon proximate the distal end. A reinforcing sleeve, having a proximal portion and a distal portion with a lumen extending therethrough, wherein the distal portion of the sleeve extends into the inflation cavity with at least a portion of the tubular member slidably disposed through the lumen thereof and the proximal portion is fixed relative to the catheter shaft and disposed in the catheter shaft inflation lumen.

21 Claims, 4 Drawing Sheets

U.S. PATENT DOCUMENTS

| | | | |
|---|---|---|---|
| 5,728,063 A | 3/1998 | Preissman et al. | |
| 5,743,875 A | 4/1998 | Sirhan et al. | |
| 5,759,173 A | 6/1998 | Preissman et al. | |
| 5,779,731 A * | 7/1998 | Leavitt | 606/194 |
| 5,820,594 A | 10/1998 | Fontirroche et al. | |
| 5,823,992 A | 10/1998 | Salmon et al. | |
| 5,868,708 A | 2/1999 | Hart et al. | |
| 5,906,606 A * | 5/1999 | Chee et al. | 604/527 |
| 6,027,477 A * | 2/2000 | Kastenhofer | 604/103.09 |
| 6,056,719 A | 5/2000 | Mickley | |
| 6,066,157 A | 5/2000 | Barbere | |
| 6,179,856 B1 | 1/2001 | Barbere | |
| 6,344,029 B1 | 2/2002 | Estrada et al. | |
| 6,475,184 B1 | 11/2002 | Wang et al. | |
| 6,530,938 B1 | 3/2003 | Lee et al. | |
| 6,626,861 B1 | 9/2003 | Hart et al. | |
| 6,648,854 B1 | 11/2003 | Patterson et al. | |
| 6,659,977 B2 * | 12/2003 | Kastenhofer | 604/96.01 |

FOREIGN PATENT DOCUMENTS

WO     WO 03/097152 A1     11/2003

* cited by examiner

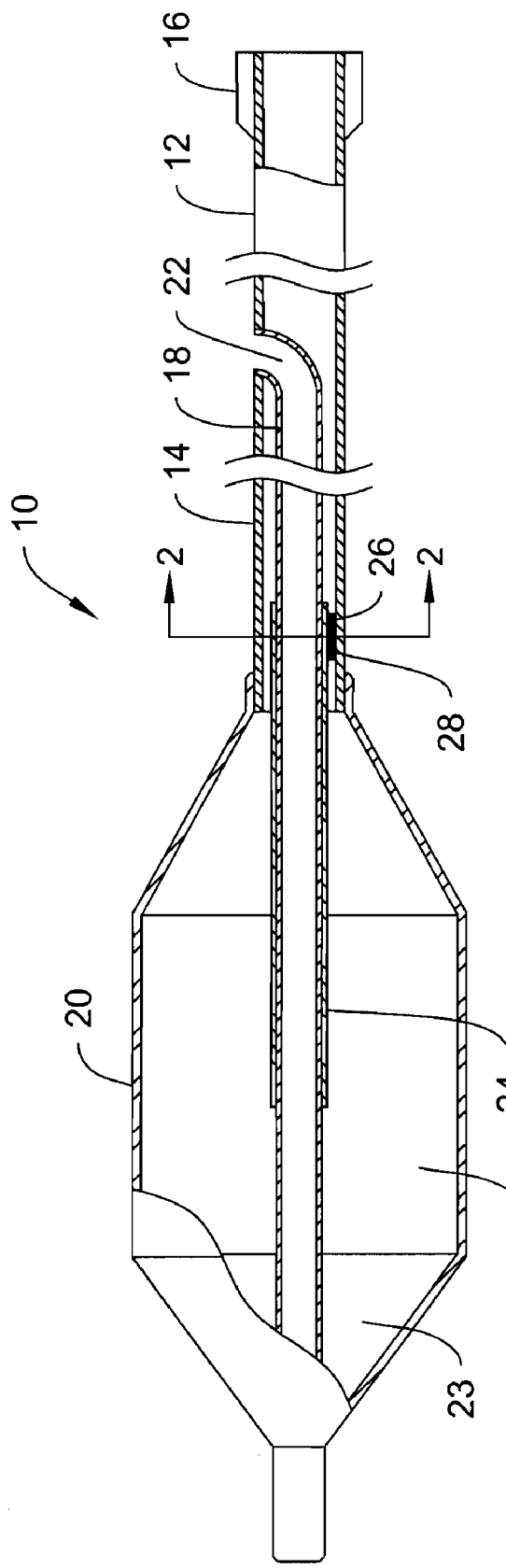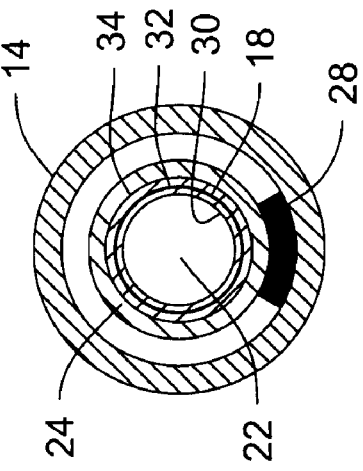

CATHETER SHAFT HAVING DISTAL SUPPORT

FIELD OF INVENTION

This invention relates generally to medical devices including balloon catheters. More specifically, the present invention relates to an improved shaft design for an angioplasty or stent delivery catheter.

BACKGROUND OF THE INVENTION

In angioplasty, a balloon catheter is generally inserted into a patient's vasculature percutaneously, usually into a femoral or radial artery. The balloon is then advanced until it reaches the treatment site, at which there is usually a stenosis or other occlusion, and expanded to compress or displace the stenosis and improve the flow of blood. In some procedures, the expandable balloon can carry a stent to be expanded at the occlusion site.

To efficiently and accurately advance a balloon catheter to a treatment site, guide catheters and guidewires are often positioned first. A balloon catheter may then be advanced over a guidewire and through a guide catheter. Consequently, a typical balloon catheter is constructed in the following manner. There is an inner tubular member having a lumen for a guidewire. This tubular member has an opening at the distal end of the balloon catheter for the introduction of the guidewire, and a more proximal opening for the egress of the guidewire. Disposed over this inner tubular member is an outer tubular member; the annular space between the first tubular member and the outer tubular member forms an inflation lumen for the balloon. A distal end of the balloon is sealed to the first tubular member and a proximal end is sealed to the outer tubular member.

The inner tubular member typically has a distal portion, often approximately the length of the balloon, that extends beyond the distal end of the outer tubular member. Thus, the distal portion of the balloon catheter may include only the distal portion of the inner tubular member and the balloon. This may make the distal end of the balloon catheter more flexible than may be desired. Also, when the balloon catheter is advanced through a patient's vasculature, much of the force resisting the advance of the balloon catheter is acting on this distal portion of the inner tubular member. This may cause the inner tubular member and the balloon to prolapse within the outer tubular member.

U.S. Pat. No. 5,425,712 to Goodin, entitled "Dilation Catheter Having Soft Bumper Tip", herein incorporated by reference, alleviates some of these issues. It discloses a catheter including the features described above. Goodin also discloses bonding the inner tubular member to a distal portion of the outer tubular member adjacent to the proximal neck portion of the balloon. This provides additional support for the distal end of the balloon catheter.

However, this also creates a balloon catheter in which both the proximal and distal ends of the balloon are fixed to the inner tubular member. It has been found that balloons grow longitudinally during inflation at least 2% and sometimes up to 10%. If the inner tubular member is not attached at the proximal end of the balloon, the entire length of the inner tubular member can accommodate this growth, resulting in a low strain that is under the elastic limit of many materials common to this application. However, if the inner tubular member is attached at the proximal end the balloon, as is the case, for example, in Goodin, only the distal section of the inner tubular member, which is a much shorter segment, is free to accommodate this growth. This results in a significantly higher strain over this distal section, and this strain may be over the elastic limit of many of the materials used in this application.

U.S. Pat. No. 6,066,157 to Barbere entitled "Anchor Joint for Coaxial Balloon Dilation Catheter" attempts to address this problem by its balloon catheter. Barbere proposes a balloon catheter having a distal balloon, an outer catheter and an inner catheter, with the inner catheter defining a guidewire lumen, and the inner and the outer catheters defining an inflation lumen. The outer tubular member tapers distally and ends near an abutment member disposed on the inner tube in the balloon. This allows the inner catheter to move distally during expansion and prevents the abutment member, and consequently the inner member, from moving proximally. The abutment member creates an area of increased stiffness in the balloon portion.

It would be desirable to provide a balloon catheter which can provide additional distal support, yet avoid higher strain on a portion of the balloon catheter.

SUMMARY OF THE INVENTION

One example embodiment pertains to a single-operator-exchange balloon catheter. The distal portion of the device has an inner tubular member, an outer tubular member and a balloon. The inner tube extends through the balloon. The distal end of the balloon is sealed to the inner tubular member, and the proximal end of the balloon is sealed to the outer tubular member. A reinforcing sleeve is slidably disposed over the inner tubular member and is attached to the outer tubular member at a distal connection point. The attachment may include a tie material. In one preferred embodiment, the reinforcing sleeve extends proximally to the distal connection point and distally into the balloon inflation cavity. Alternatively, the reinforcing sleeve may extend to near the distal end of the balloon, and may extend further proximally. In another alternative embodiment, the reinforcing sleeve extends to the balloon tip. A single bond area including the inner shaft, reinforcing sleeve and distal balloon waist can then be utilized to improve pushability and column strength.

Another example embodiment pertains to an over-the-wire balloon catheter. The distal portion of the device has an inner tubular member, an outer tubular member and a balloon wherein the inner tubular member extends through the balloon. A reinforcing tubular member is attached to the outer tubular member and slidably disposed over the inner tubular member, and may extend distally to the distal balloon cone.

The above summary of some embodiments is not intended to describe each disclosed embodiment or every implementation of the present invention. The Figures, and Detailed Description which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is a partial plan view with cross-sections of an example single-operator-exchange balloon catheter;

FIG. 2 is a cross-sectional view of the catheter of FIG. 1 taken along line 2-2;

DETAILED DESCRIPTION OF EMBODIMENTS

Figure 3:
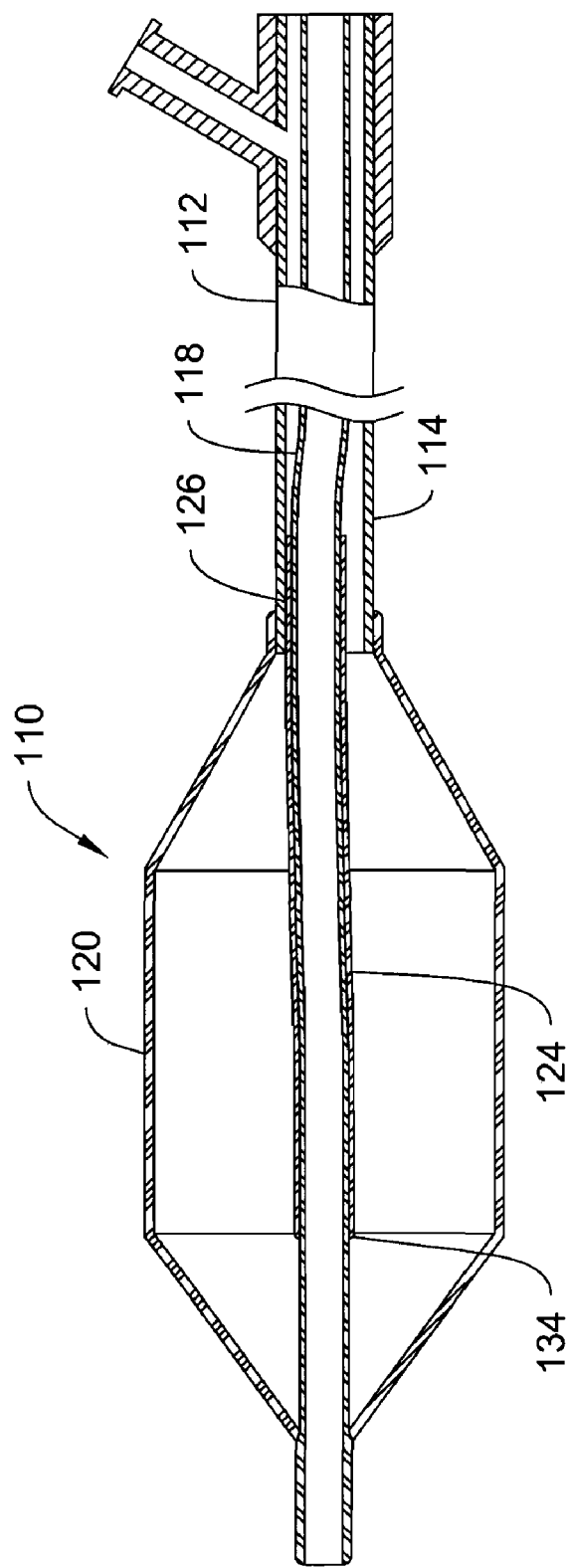
FIG. 3 is a partial cross-sectional view of an example over-the-wire catheter.

The following description should be read with reference to the drawings wherein like reference numerals indicate like elements throughout the several views. The drawings, which are not necessarily to scale, depict illustrative embodiments of the claimed invention.

FIG. 1 is a partial plan view with portions in cross-section of an example single-operator-exchange balloon catheter 10 having a proximal end 12 with an outer tubular lo member 14 and a proximal hub assembly 16. Balloon catheter 10 may be used for an angioplasty procedure, a stent delivery procedure, or other therapeutic technique. An inner tubular member 18 is introduced through a wall of outer tubular member 14 and extends distally past a balloon 20. Outer tubular member 14 may terminate distally proximate the proximal end of balloon 20, and the proximal end of balloon 20 may be sealed to outer tubular member 14. The distal end of balloon 20 may be sealed to inner tubular member 18. A lumen 22 of inner tubular member 18 may be a guidewire lumen. Of course, while tubular member 14 is called an outer tubular member, and tubular member 18 is called an inner tubular member, these terms are not meant to imply that tubular member 14 must be the outermost tube and tubular member 18 must be the innermost tube. While this configuration is contemplated and described herein, other configurations with one or more tubular members outside tubular member 14 or inside tubular member 18 are also contemplated. Slidably disposed on inner tubular member 18 is a reinforcing sheath 24. Reinforcing sheath 24 may extend from a point proximate the distal end of the outer tubular member 14 distally into the balloon 20 inflation cavity 21 or into a distal cone 23 of balloon 20 or other desired location. For example, reinforcing sheath 24 may extend halfway into the balloon 20 inflation cavity, may extend to the distal balloon cone, or may extend into the balloon cone. Reinforcing sheath 24 and inner tubular member 18 may be axially aligned with the center of the lumen of outer tubular member 14 or may be offset toward one wall, if desired.

In one preferred embodiment, reinforcing sheath 24 is attached to outer tubular member 14 at an attachment point 26. FIG. 2 is a cross-sectional view of balloon catheter 10 at attachment point 26. In this embodiment, an adhesive 28 is provided between outer tubular member 14 and reinforcing sheath 24 at attachment point 26. Adhesive 28 may occupy part of the annular lumen between reinforcing sheath 24 and outer tubular member 14 to provide stability to the bond between the sheath and the tubular member, and may also leave the substantial part of the lumen free for rapid inflation and deflation. In this way, the size of the inflation lumen may be optimized. Alternatively, a heat bond could be utilized.

Attachment point 26 may be at any point distal the proximal end of inner tubular member 18 and proximal the distal end of outer tubular member 14. It may, for example, be proximate the distal end of outer tubular member 14 as shown in FIG. 1. Reinforcing sheath 24 may terminate proximally at or near attachment point 26 or may continue proximally past attachment point 26 to alter the flexibility and stiffness of balloon catheter 10. For example, referring to FIG. 2, reinforcing sheath 24 may extend 20-25 cm into outer tubular member 114, or other suitable distance.

The term "slidably" is herein defined to mean both a loose fit between the inner tubular member and the reinforcing sheath where the diameter of the inner surface of reinforcing sheath 24 is as large or larger than the diameter of the outer surface of inner tubular member 18 and also certain configurations where the diameter of the inner surface of reinforcing sheath 24 is smaller than the diameter of the outer surface of inner tubular member 18 provided that the tubular member may slide within the reinforcing sheath prior to reaching plastic deformation and return to an unstrained position when the balloon is deflated. There may, of course, also be a gap between reinforcing sheath 24 and tubular member 18, if desired.

FIG. 3 is a cross-sectional view of an example over-the-wire balloon catheter 110. Balloon catheter 110 has an inner tubular member 118 extending proximally within outer tubular member 114 to proximal end 112 in an over-the-wire fashion, but is otherwise similar to balloon catheter 10 except for differences herein pointed out. In balloon catheter 110, reinforcing sheath 124 is bonded to outer tubular member 114 at attachment point 126. This bonding may be done by laser welding or other suitable method. This bonding may require reinforcing sheath 124 and inner tubular member 118 to be axially offset with respect to the center of the lumen of outer tubular member 114 at the attachment point 126. The diameter of the inner surface of reinforcing member 124 may be slightly larger than the diameter of the outer surface of inner tubular member 118. Reinforcing member 124 may extend distally into the distal cone of balloon 120 and may extend to the distal joint between balloon 120 and inner member 118. Reinforcing member 124 may have a distally tapering distal end 134.

Figure 4:
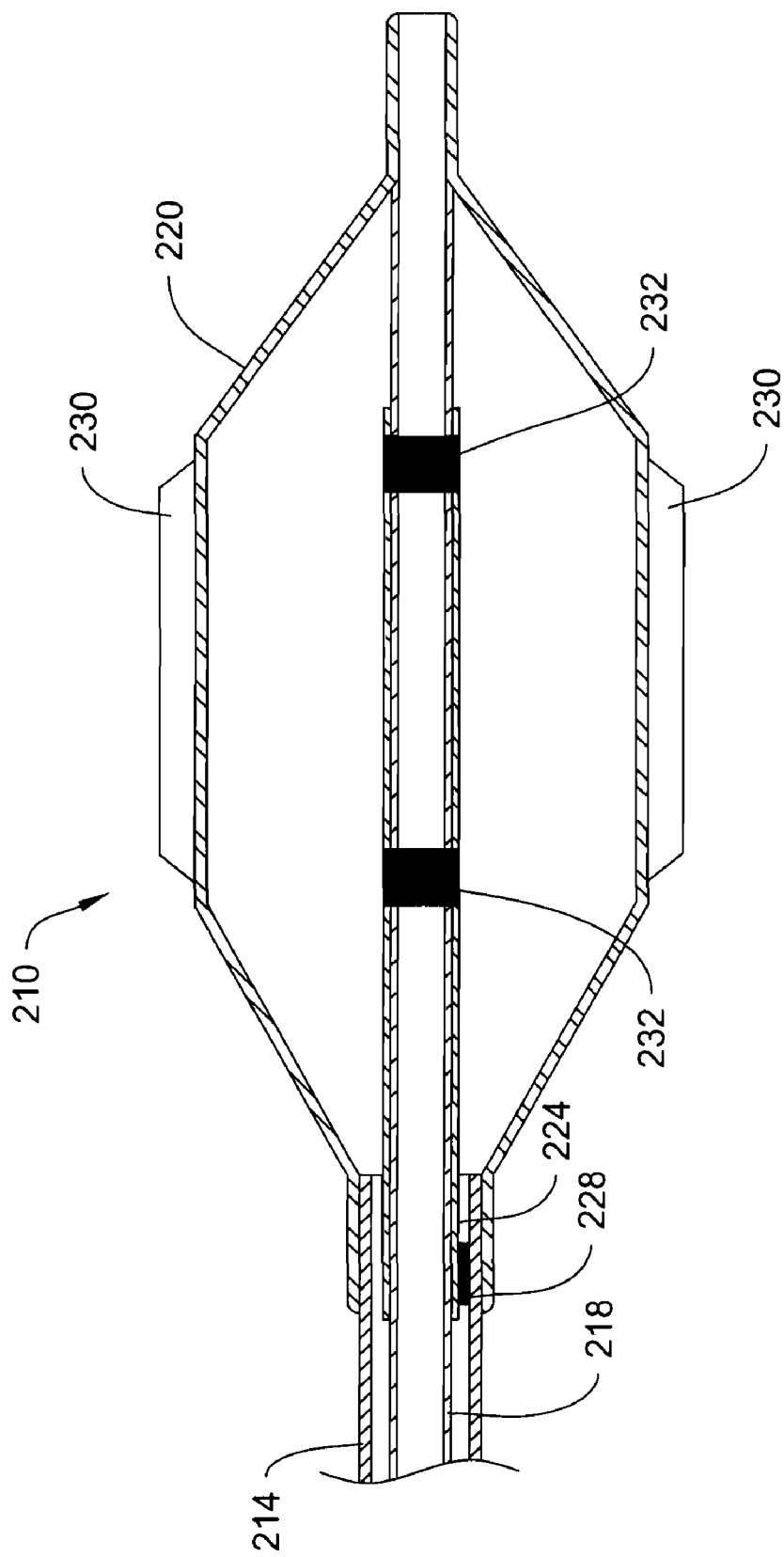
FIG. 4 is a partial cross-sectional view of an example cutting balloon catheter.

FIG. 4 is a partial cross-sectional view of the distal portion of an example cutting balloon catheter 210. Cutting balloon catheter 210 includes outer tubular member 214, inner tubular member 218 and cutting balloon 220 with cutting surfaces 230. Slidably disposed over inner tubular member 218 and extending distally into balloon 220 cavity is reinforcing member 224. Reinforcing member 224 is fixed to outer tubular member 214 by adhesive 228. Radiopaque markers 232 may be disposed on reinforcing member 224 or at other desired locations.

Figure 5:
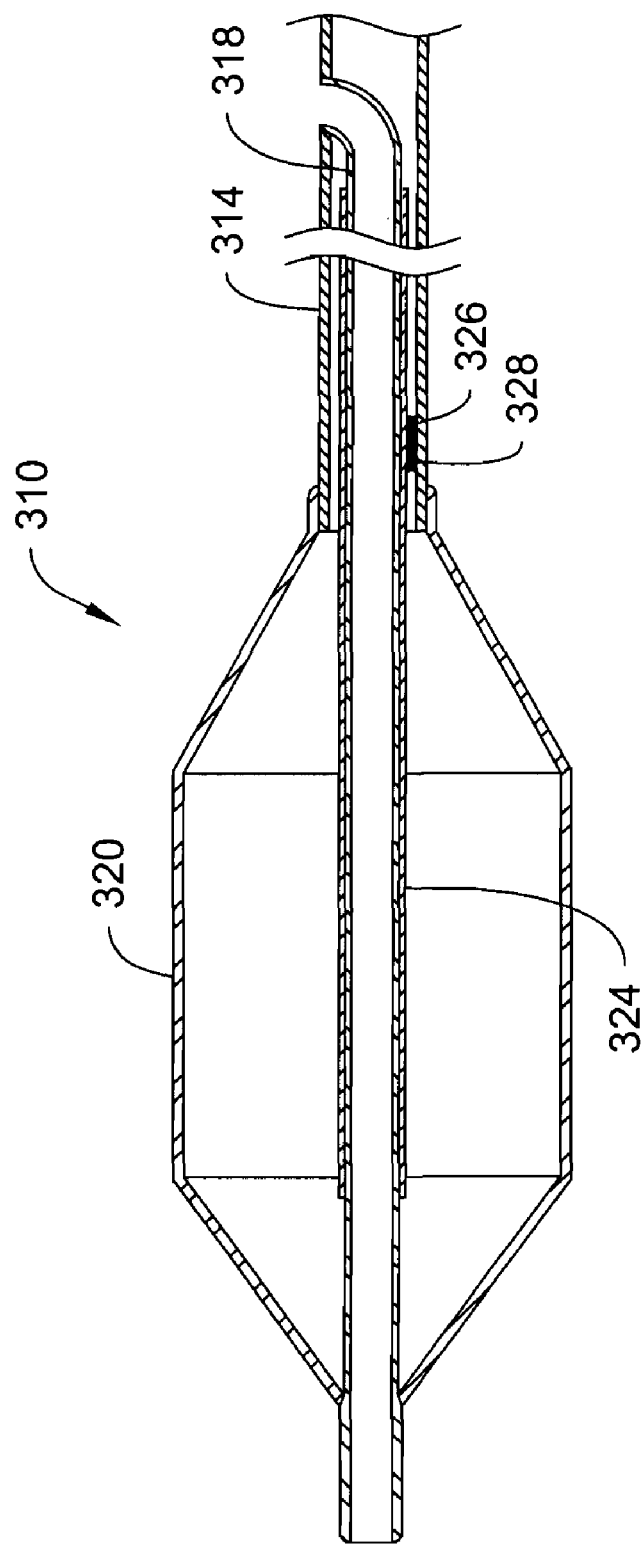
FIG. 5 is a partial cross-sectional view of an alternative single-operator exchange catheter.

FIG. 5 is a partial cross-sectional view of the distal portion of another example single-operator-exchange balloon catheter 310. Balloon catheter 310 has an outer tubular member 314, an inner tubular member 318 and a balloon 320. A reinforcing member 324 is disposed over inner tubular member 318 and extends distally to proximate the distal end of balloon 320 and proximally past attachment point 326. Reinforcing sheath may extend proximally past attachment point 326 1-25 cm, 1-20 cm, 1-10 cm, or 1-5 cm.

The balloon may be made from typical angioplasty balloon materials including polymers such as polyethylene terephthalate (PET), polyetherimide (PEI), polyethylene (PE), etc. Some other examples of suitable polymers, including lubricious polymers, may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP.

The inner and outer tubular members may be manufactured from a number of different materials. For example, the tubular members may be made of metals, metal alloys, polymers, metal-polymer composites or any other suitable materials. Some examples of suitable metals and metal alloys include stainless steel, such as 300 series stainless steel (including 304V, 304L, and 316L; 400 series martensitic stainless steel; tool steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable materials. Some examples of suitable polymers include those described above in relation to balloon 16. Of course, any other polymer or other suitable materials including ceramics may be used without departing from the spirit of the invention. The materials used to manufacture inner tubular member 18 may be the same as or be different from the materials used to manufacture outer tubular member 14. Of course, a tubular member may incorporate layers or blends of certain polymers to get certain properties. For example, the inner tubular member 18 may have a high density polyethylene inner layer 30, a polyether block amide polymer outer layer 34, and a linear low density polyethylene tie layer 32 between the inner layer 30 and the outer layer 34.

The reinforcing sheath may be made from any of the materials described above to with respect to the tubular members, or it may be made from other materials. In preferred embodiments, the reinforcing sleeve is elastic (recovers all or almost all the imposed strain up to about 10%). The material of construction is preferably an elastomer or elastomer-based material. An example of an elastomer is Kraton G1657, a relatively stiff styrene-butadiene polymer from Kraton Polymers or, alternatively, PEBAX® 7233 or 7033. An elastomer-based material can include a composite of a brittle polymer and softer elastomer. The reinforcing sheath may be extruded separately and assembled onto the inner tubular member or may be coextruded with the inner tubular member.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A catheter comprising:
an inflatable balloon having a proximal end, a distal end, and an inflation cavity therebetween;
a catheter shaft having the inflatable balloon affixed proximate a distal end thereof, the catheter shaft having an inflation lumen fluidly connected to the balloon inflation cavity and a guidewire lumen extending through the balloon cavity within a tubular member which is affixed to the inflatable balloon proximate the distal end; and
a reinforcing sleeve, having a proximal portion and a distal portion with a lumen extending therethrough, wherein the distal portion of the reinforcing sleeve extends into the inflation cavity with at least a portion of the tubular member slidably disposed through the lumen of the reinforcing sleeve and the proximal portion of the reinforcing sleeve is fixed relative to the catheter shaft and disposed in the catheter shaft inflation lumen.
2. The catheter of claim 1, wherein the catheter shaft comprises an outer member, wherein the reinforcing sleeve is attached to the outer member at a tack point.
3. The catheter of claim 2, wherein the reinforcing sleeve extends proximally to the tack point.
4. The catheter of claim 2, wherein the reinforcing sleeve extends proximally past the tack point.
5. The catheter of claim 4, wherein the reinforcing sleeve extends at least 15 cm proximally past the tack point.
6. The catheter of claim 1, wherein the catheter shaft comprises a guidewire receiving tube defining the guidewire lumen and having an outer diameter, wherein the reinforcing sleeve has an inner diameter that is at least as great as the outer diameter of the guidewire receiving tube.
7. The catheter of claim 1, wherein the guidewire receiving tube outer diameter is substantially the same as the reinforcing sleeve inner diameter.
8. The catheter of claim 1, wherein the guidewire receiving tube outer diameter is slightly greater than the reinforcing sleeve inner diameter.
9. The catheter of claim 1, wherein the reinforcing sleeve extends into the distal waist of the inflatable balloon.
10. The catheter of claim 1, wherein the reinforcing sleeve extends at least halfway through the inflation cavity.
11. A catheter comprising:
a guidewire tube having a distal end, a proximal end, a lumen therebetween, and an outer surface;
an outer tube disposed over the guidewire tube, the outer tube having a distal end, a proximal end and an inner surface defining a lumen therebetween;
a balloon having a distal waist sealingly fixed to the guidewire tube, a proximal waist sealingly fixed to the outer tube, and an inflation cavity therebetween; and
a reinforcing sleeve having an outer surface attached to the inner surface of the outer tube and extending distally into the inflation cavity;
wherein the guidewire tube is slidably disposed within the reinforcing sleeve.
12. The catheter of claim 11, wherein the guidewire tube comprises an inner lubricious layer and an outer layer.
13. The catheter of claim 12, further comprising a tie layer between the inner lubricious layer and the outer layer.
14. The catheter of claim 11, wherein the reinforcing sleeve includes an inner surface, wherein the inner surface of the reinforcing sleeve is in contact with the outer surface of the guidewire tube.
15. A catheter comprising:
a first elongate member having a proximal end, a distal end, and a lumen therebetween;

a second elongate member partially disposed in the lumen of the first elongate member having a proximal end, a distal end, and a lumen therebetween;

a third elongate member disposed on the second elongate member, the third elongate member having a distal end, a proximal end, and a lumen therebetween; and an inflatable balloon member disposed on the second elongate member, the inflatable balloon member having a distal end, a proximal end, and a lumen therebetween;

wherein the distal end of the inflatable balloon member is sealingly connected to an outer surface of the second elongate member and wherein a proximal portion of the inflatable balloon member is sealingly connected to a first distal portion of the first elongate member;

wherein the third elongate member extends from a point proximal the distal end of the first elongate member to a point distal the proximal end of the balloon;

wherein a portion of the third elongate member proximate the balloon is fixed to a distal portion of the first elongate member; and wherein the second elongate member is slidably disposed within the third elongate member.

16. The catheter of claim 15, wherein the proximal end of the third elongate member is proximate the proximal end of the balloon.

17. The catheter of claim 15, wherein the proximal end of the third elongate member is proximate the proximal end of the second elongate member.

18. The catheter of claim 15, wherein the third elongate member comprises an elastic material.

19. The catheter of claim 15, further comprising a tie material connecting the third elongate member to the first elongate member.

20. The catheter of claim 15, wherein the third elongate member is fused to the first elongate member.

21. The catheter of claim 15, wherein the second elongate member has a first outer diameter extending from proximate the proximal end of the third elongate member to proximate the distal end of the balloon.

* * * * *

UNITED STATES PATENT AND TRADEMARK OFFICE
CERTIFICATE OF CORRECTION

| | | |
|---|---|---|
| PATENT NO. | : 7,491,213 B2 | Page 1 of 1 |
| APPLICATION NO. | : 10/757683 | |
| DATED | : February 17, 2009 | |
| INVENTOR(S) | : Daniel Perreault and Douglas A. Devens, Jr. | |

It is certified that error appears in the above-identified patent and that said Letters Patent is hereby corrected as shown below:

Column 3
Line 19: after tubular and before member, delete "lo".

Column 4
Line 37: delete "2l0" and insert therefor -- 210 --.

Signed and Sealed this

Twenty-sixth Day of May, 2009

JOHN DOLL
*Acting Director of the United States Patent and Trademark Office*